United States Patent [19]

de Rijke

[11] 3,948,814

[45] Apr. 6, 1976

[54] ACETALDEHYDE ETHYL LINALYL ACETAL PERFUME COMPOSITIONS

[75] Inventor: David de Rijke, Naarden, Netherlands

[73] Assignee: Naarden International, N.V., Naarden-Bussum, Netherlands

[22] Filed: Aug. 10, 1972

[21] Appl. No.: 279,297

[30] Foreign Application Priority Data

Aug. 11, 1971 Netherlands ........................ 7111071

[52] U.S. Cl. ............................. 252/522; 260/615 A

[51] Int. Cl.[2] ...................... A61K 7/46; C07C 43/30

[58] Field of Search .................. 252/522; 260/615 A

[56] References Cited

FOREIGN PATENTS OR APPLICATIONS 821,203 11/1951 Germany ........................... 252/522

OTHER PUBLICATIONS

Shostakovskii, Chem. Abs., Vol. 41, 1947, p. 1999*c*.

Keller, Chem. Abs., Vol. 55, 1961, p. 19983*e*.

Moncrieft, The Chem. of Perf. Mat. United Trade Press, London, 1949, pp. 314–315.

*Primary Examiner*—Jerome D. Goldberg
*Assistant Examiner*—A. P. Fagelson
*Attorney, Agent, or Firm*—Stevens, Davis, Miller & Mosher

[57] ABSTRACT

Odorous acetaldehyde ethyl linalyl acetal, perfume compositions, materials or products comprising conventional constituents such as solvents, diluents and adjuvants and containing as an essential ingredient acetaldehyde ethyl linalyl acetal. Also the method of preparing perfume compositions by adding the acetal thereto and the method of preparing the acetal by reacting a solution of sulfuric acid in linalool to vinylethyl ether, adding soda thereto, separating and fractionating an organic layer with soda.

2 Claims, No Drawings

ACETALDEHYDE ETHYL LINALYL ACETAL PERFUME COMPOSITIONS

The invention relates to a process for the preparation of perfume compositions and perfumed products, which contain in addition to conventional constituents usual for this purpose an odorous component acetaldehyde ethyl linalyl acetal of the formula:

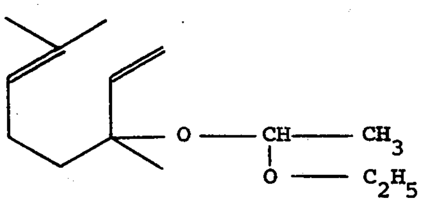

Acetaldehyde ethyl linalyl acetal is a novel commpound not previously described in the literature. Acetaldehyde butyl linalyl acetal, an analogous compound has been described in Zh. Obshch. Khim. 16 (1946) 937–951 (Chem. Abstr. 41 (1947) 1999*c*) and in Sin. Org. Soedin 2 (1952) 154–161 (Chem. Abstr. 48 (1954) 569*c*), but without mention of odorous properties, if any. Acetaldehyde ethyl linalyl acetal acts as an intermediate product in the synthesis of 5.9-dimethyl-4.8-decadiene-1-al even though it has not been mentioned particularly and has not been isolated. (see Helv. Chim. Acta 50 (1967) 2095–2100 and the German "Auslegeschrift" 1,193,490, example 15).

This aldehyde is formed by rearrangement from acetaldehyde ethyl linalyl acetal and has a fatty, somewhat fruity odor, reminiscent of lauryl and tetradecylaldehyde.

It surprisingly now has been found that acetaldehyde ethyl linalyl acetal has an exalting flower odor, related to the odor of hydroxy citronellal. Thus, this acetal is very suitable for perfume compositions having a flower odor like rose, freesia and lily of the valley, as well as for giving a flowerlike undertone to other compositions. The acetal may be employed in quantities of from 10–15 percent by weight of the composition. However, the quantity may be varied dependent upon the perfumer and the ultimate aroma desired.

The preparation of acetaldehyde ethyl linalyl acetal can be carried out by the addition of linalool to vinylethyl ether (see German Auslegeschrift No. 1,193,490 and Zh. Obshch. Khim 16 (1946) 937–951). The following Example illustrates the preparation of acetaldehyde ethyl linalyl acetal.

EXAMPLE I

Into an 1 l reaction flask is placed 216 g vinylethyl ether. Under stirring a solution of 0.2 g concentrated sulfuric acid (s.g. 1.84) in 154 g linalool is added over a 2 hour period at 30°C. Then 100 g of a 10-percent soda solution are added to the reaction mixture and the entire mixture is stirred for half an hour. The organic upper layer is separated and fractionated with 0.5 g soda to obtain 186 g acetaldehyde ethyl linalyl acetal. The acetal has a boiling point of 90°–94°C. at 2 mm Hg; $n_D^{20}$ 1,4495–1,4485. The addition of soda to the product to be distilled prevents the formation of 5.9-dimethyl-4.8-decadien-1-al during the fractionation.

The following Examples illustrate perfume compositions prepared according to this invention using the acetaldehyde ethyl linalyl acetal of Example I.

EXAMPLE II

| Perfume composition "freesia". | |
|---|---|
| Dodecanal, 10% in diethylphthalate | 10 parts by weight |
| so-called aldehyde C14, 10% in diethylphthalate | 20 parts by weight |
| so-called aldehyde C17, 10% in diethylphthalate | 5 parts by weight |
| isojasmone | 30 parts by weight |
| methylphenyl carbinyl acetate | 10 parts by weight |
| lemon oil Italian | 20 parts by weight |
| bergamot oil of Reggio | 100 parts by weight |
| tetrahydrolinalool | 140 parts by weight |
| hydroxycitronellal | 45 parts by weight |
| laevo-citronellol | 100 parts by weight |
| 2-phenylethanol | 55 parts by weight |
| geraniol | 55 parts by weight |
| ylang ylang oil I | 10 parts by weight |
| α-methyl jonone | 100 parts by weight |
| benzyl acetate | 60 parts by weight |
| α-hexylcinnamic aldehyde | 50 parts by weight |
| heliotropin | 30 parts by weight |
| musk ambrette | 10 parts by weight |
| acetaldehyde ethyl linalyl acetal | 150 parts by weight |
| | 1000 parts by weight |

EXAMPLE III

| Soap perfume (phantasy flowerlike aldehyde). | |
|---|---|
| undecylene aldehyde, 10% in diethylphthalate | 30 parts by weight |
| methylnonylacetaldehyde, 10% in diethylphthalate | 30 parts by weight |
| methylphenyl carbinylacetate | 20 parts by weight |
| hydroxycitronellal | 150 parts by weight |
| laevo-citronellol | 50 parts by weight |
| α-hexylcinnamic aldehyde | 25 parts by weight |
| 2-phenylethanol | 50 parts by weight |
| geraniol | 35 parts by weight |
| phenylacetaldehyde, 10% in diethylphthalate | 15 parts by weight |
| α-methyljonone | 100 parts by weight |
| benzylacetate | 75 parts by weight |
| 4-tert. butylcyclohexylacetate | 100 parts by weight |
| hexylbenzoate | 100 parts by weight |
| linalylacetate | 40 parts by weight |
| eugenol | 20 parts by weight |
| ylang ylang oil II | 30 parts by weight |
| musk ambrette | 20 parts by weight |
| 11-oxahexadecanolide | 10 parts by weight |
| acetaldehyde ethyl linalyl acetal | 100 parts by weight |
| | 1000 parts by weight |

What I claim is:

1. A perfume composition comprising a mixture of perfumery materials including acetaldehyde ethyl linalyl acetal in an amount sufficient to give a flowerlike undertone to said composition.

2. The perfume composition of claim 1 containing from 10–15 percent by weight of acetaldehyde ethyl linalyl acetal.

* * * * *